United States Patent
Kim et al.

(10) Patent No.: US 9,458,079 B2
(45) Date of Patent: Oct. 4, 2016

(54) HETEROGENEOUS CATALYST FOR PREPARING ACRYLIC ACID FROM ALLYL ALCOHOL, AND METHOD OF PREPARING ACRYLIC ACID FROM ALLYL ALCOHOL USING THE SAME

(71) Applicants: LG CHEM, LTD., Seoul (KR); Industry-Academic Cooperation Foundation, Yonsei University, Seoul (KR)

(72) Inventors: Dae Sung Kim, Daejeon (KR); Won Jae Lee, Daejeon (KR); Yong-Jin Choe, Daejeon (KR); Myungjin Kong, Daejeon (KR); Hyunjoo Lee, Daejeon (KR); Sungpil Yang, Seoul (KR)

(73) Assignees: LG CHEM, LTD., Seoul (KR); Industry-Academic Cooperation Foundation, Yonsei University, Seoul (KR)

( * ) Notice: Subject to any disclaimer, the term of this patent is extended or adjusted under 35 U.S.C. 154(b) by 0 days.

(21) Appl. No.: 14/527,314

(22) Filed: Oct. 29, 2014

(65) Prior Publication Data

US 2015/0361021 A1    Dec. 17, 2015

(30) Foreign Application Priority Data

Jun. 16, 2014  (KR) .................. 10-2014-0072844

(51) Int. Cl.
| | | |
|---|---|---|
| C07C 51/00 | (2006.01) | |
| C07C 51/25 | (2006.01) | |
| B01J 23/66 | (2006.01) | |
| B01J 35/00 | (2006.01) | |

(52) U.S. Cl.
CPC ............... *C07C 51/25* (2013.01); *B01J 23/66* (2013.01); *B01J 35/006* (2013.01); *B01J 35/0013* (2013.01)

(58) Field of Classification Search
CPC ................................ C07C 51/25; B01J 23/52
See application file for complete search history.

(56) References Cited

FOREIGN PATENT DOCUMENTS

| | | |
|---|---|---|
| WO | 2008/092115 | 7/2008 |
| WO | 2010110447 A1 | 9/2010 |

OTHER PUBLICATIONS

Della Pina, Cristina; Falletta, Ermelinda; Rossi, Michele; ChemSusChem (2009), 2(1), 57-58.*
Della Pina, et al., ChemSusChem 2009, 2, 57-58.*
Falletta E et al."Enhanced performance of the catalytic conversion of allyl alcohol to 3-hydroxypropionic acid using bimetallic gold catalysts.," Faraday Discuss, 2012, vol. 152, pp. 367-379.
Mario G. Clerici, et al., "Liquid Phase Oxdiatio via Heterogeneous Catalysis," Wiley, 2013.
"A green approach to chemical build-ing blocks. The case of 3-hydroxypropanoic acid," ; Pina, et al.; Green Chem., 2011, 13, pp. 1624-1632.
"Oxidation of Allyl Alcohol in the Presence of a Gold Catalyst: A Route to 3-Hydroxypropionic Acid."; Pina, et al. ChemSusChem 2009, 2, pages 57-58.
"Active Nonmetallic Au and Pt Species on Ce-ria-Based Water-Gas Shift Catalysts," ; Fu, et al.; Science 301, 2003, pp. 935-938.

* cited by examiner

*Primary Examiner* — Porfirio Nazario Gonzalez
*Assistant Examiner* — Kofi Adzamli
(74) *Attorney, Agent, or Firm* — Dentons US LLP

(57) ABSTRACT

The present invention relates to a heterogeneous catalyst for preparing acrylic acid from allyl alcohol, and a method of preparing acrylic acid from allyl alcohol using the same. More particularly, the present invention relates to a method of preparing acrylic acid from allyl alcohol at a high yield by performing a liquid phase reaction in the presence of a heterogeneous catalyst including gold supported on a carrier.

3 Claims, 4 Drawing Sheets

Synthesized for 1hr
Au size : < 1nm
(2.7 wt%)

Synthesized for 2hr
Au size : < 1nm
(2.6 wt%)

Synthesized for 3hr
Au size : 1.9 ± 0.3 nm
(3.4 wt%)

Synthesized for 6hr
Au size : 2.9 ± 0.5 nm
(3.6 wt%)

HETEROGENEOUS CATALYST FOR PREPARING ACRYLIC ACID FROM ALLYL ALCOHOL, AND METHOD OF PREPARING ACRYLIC ACID FROM ALLYL ALCOHOL USING THE SAME

CROSS REFERENCE TO RELATED APPLICATION

This application claims the benefit of Korean Patent Application No. 10-2014-0072844, filed Jun. 16, 2014, which is hereby incorporated by reference in its entirety into this application.

BACKGROUND OF THE INVENTION

1. Technical Field

The present invention relates to a heterogeneous catalyst for preparing acrylic acid from allyl alcohol, and a method of preparing acrylic acid from allyl alcohol using the same. More particularly, the present invention relates to a method of preparing acrylic acid from allyl alcohol at a high yield by performing a liquid phase reaction in the presence of a heterogeneous catalyst including gold supported on a carrier.

2. Description of the Related Art

Acrylic acid is the simplest unsaturated carboxylic acid, and is a main raw material of superabsorbent polymers (SAPs) which are synthetic polymer materials having a capacity for absorbing 500 to 1000 times their own weight in moisture. SAPs started to be put to practical use in sanitary items, and, currently, are widely used as raw materials in soil conditioners for horticulture, water stopping agents for civil engineering and construction applications, sheets for raising seedlings, freshness preservatives for food distribution, goods for fomentation, and the like, in addition to sanitary items such as disposable diapers for children. Therefore, SAPs, known to have superior water absorbency as compared to conventional water-absorbing polymers, become increasingly more widely used in practical applications, and thus their market values become higher. Further, acrylic acid, used as a raw material of SAPs, has an important market value, too. Additionally, acrylic acid is used as an essential raw material of various kinds (3000 or more) of goods, such as acrylic fibers, paints, adhesives, coating agents and the like.

Currently, as a method of producing acrylic acid, a process of producing acrylic acid from propylene obtained from fossil fuel is generally used.

Meanwhile, glycerol is produced as a by-product in the process of producing a biodiesel from vegetable oils. In this case, when acrylic acid is produced from allyl alcohol derived from glycerol, there is an advantage in that acrylic acid can be produced from environment-friendly biomass without using fossil fuel. WO 2008/092115 A discloses a method of obtaining allyl alcohol, wherein allyl alcohol can be obtained by the reaction of glycerol and formic acid, without a catalyst, at a high yield. Therefore, it is expected that, when acrylic acid is produced from allyl alcohol, glycerol, as a by-product of biodiesel, can be effectively used, and thus the economical efficiency of biodiesel can be increased, and acrylic acid can be effectively produced from glycerol.

Therefore, research into the method of preparing acrylic acid from allyl alcohol at a high yield using special synthesis conditions is required.

PRIOR ART DOCUMENTS

Patent Document (Patent document 1) WO 2008/092115 A1

Nonpatent Documents (Nonpatent document 1) Green Chem. 2011, 13, 1624-1632
(Nonpatent document 2) Chem Sus Chem, 2009, 2, 57-58
(Nonpatent document 3) Science 301, 2003, 935-938

SUMMARY OF THE INVENTION

Accordingly, the present invention has been devised to solve the above-mentioned problems, and an object of the present invention is to provide a method of preparing acrylic acid from allyl alcohol at a high yield by performing a liquid phase reaction in the presence of a heterogeneous catalyst including gold supported on a carrier.

In order to accomplish the above object, an aspect of the present invention provides a heterogeneous catalyst for preparing acrylic acid from allyl alcohol, wherein the catalyst includes gold having a particle size of 5 nm or less supported on a carrier.

Another aspect of the present invention provides a method of preparing acrylic acid from allyl alcohol, including the steps of: a) introducing the heterogeneous catalyst including gold having a particle size of 5 nm or less supported on a carrier into a mixed solution of a basic solution and allyl alcohol; b) injecting oxygen-containing gas into a reactor filled with the mixed solution and then reacting the mixed solution under the condition of the partial pressure of oxygen in the reactor being 1 to 50 bar, based on absolute pressure, and the temperature in the reactor being 30 to 100° C. so as to obtain a liquid reaction product containing acrylic acid; and c) separating acrylic acid from the liquid reaction product.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Figure 1A:
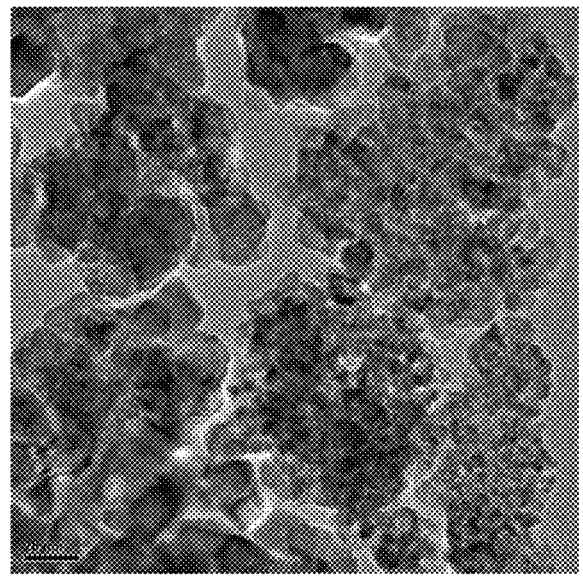
FIGS. 1A to 1D show the photographs of the heterogeneous catalyst prepared in Example 1, taken using a transmission electron microscope (JEM-2100, JEOL), wherein cerium oxide ($CeO_2$) was used as a carrier, the sizes of gold particles supported on the carrier are shown according to catalyst synthesis time, and the weight percentages (wt %) of gold particles based on the total weight of the carrier are shown, respectively.

Hereinafter, a heterogeneous catalyst for preparing acrylic acid from allyl alcohol according to the present invention and a method of preparing acrylic acid from allyl alcohol using the same according to the present invention will be described in detail.

The present invention relates to a method of preparing acrylic acid from allyl alcohol at a high yield using special synthesis conditions. Therefore, according to this method, acrylic acid can be produced at a remarkably high yield compared to that of conventional methods.

1. Heterogeneous Catalyst for Preparing Acrylic Acid from Allyl Alcohol

The term "heterogeneous catalyst" used herein means that the phase of a reactant is different from that of a catalyst, and the use of the heterogeneous catalyst has the advantage in that a catalyst can be easily separated from a reaction mixture. For this purpose, the heterogeneous catalyst for preparing acrylic acid from allyl alcohol according to the present invention is characterized in that gold having a particle size of 5 nm or less supported on a carrier, preferably, 1 nm or less. When the size of gold particles is present within the above range, the heterogeneous catalyst exhibits excellent reactivity and selectivity. Further, as the size of gold particles decreases, the yield of acrylic acid and 3-hydroxypropionic acid (3-HPA), as products, increases. In particular, when the size of gold particles is 1 nm or less, the yield of acrylic acid, as a main product, reaches 50%, which is more preferable.

Further, gold may be included in an amount of 5 wt % or less, preferably, 0.0001 to 5 wt %, based on the total dry weight of the carrier. When the amount of gold is present within the above range, there is an advantage in that the usage of gold as a precious metal can be minimized, and simultaneously the reactivity of the heterogeneous catalyst can be maximized.

The carrier may include at least one selected from the group consisting of activated carbon, titanium oxide ($TiO_2$), aluminum oxide ($Al_2O_3$), silicon oxide ($SiO_2$), zinc oxide ($ZnO_2$), zirconium oxide ($ZrO_2$), manganese oxide ($MnO_2$), iron oxide ($Fe_2O_3$), vanadium oxide ($V_2O_5$), tin oxide ($SnO_2$), tungsten oxide ($WO_3$) and cerium oxide ($CeO_2$). More preferably, the carrier may include the cerium oxide ($CeO_2$) or a composite oxide containing cerium oxide ($CeO_2$).

2. Method of Preparing Acrylic Acid from Allyl Alcohol

In the method of preparing acrylic acid according to the present invention, commercially available allyl alcohol may be used without limitation as long as it can be used in preparing acrylic acid. Preferably, allyl alcohol having a purity of 60 to 99.9% may be used in preparing acrylic acid.

The method of preparing acrylic acid from allyl alcohol according to the present invention includes the steps of: a) introducing a heterogeneous catalyst including gold having a particle size of 5 nm or less supported on a carrier into a mixed solution of a basic solution and allyl alcohol; b) injecting oxygen-containing gas into a reactor filled with the mixed solution and then reacting the mixed solution under the condition of the partial pressure of oxygen in the reactor being 1 to 50 bar based on absolute pressure and the temperature in the reactor being 30 to 100° C. to obtain a liquid reaction product containing acrylic acid; and c) separating acrylic acid from the obtained liquid reaction product.

More specifically, in the method of preparing acrylic acid from allyl alcohol according to the present invention, as the heterogeneous catalyst for preparing acrylic acid from allyl alcohol, a catalyst including a gold supported on a carrier having a particle size of 5 nm or less, preferably, 1 nm or less may be used. When the particle size of gold is present within the above range, the heterogeneous catalyst exhibit excellent reactivity and selectivity. Further, as the particle size of gold decreases, the yield of acrylic acid and 3-hydroxypropionic acid (3-HPA), as products, increases. In particular, when the particle size of gold is 1 nm or less, the yield of acrylic acid, as a main product, reaches 50%, which is more preferable.

Further, gold may be included in an amount of 5 wt % or less, preferably, 0.0001 to 5 wt %, based on the total dry weight of the carrier. When the amount of gold is present within the above range, there is an advantage in that the usage of gold as a precious metal can be minimized, and simultaneously the reactivity of the heterogeneous catalyst can be maximized.

The carrier may include at least one selected from the group consisting of activated carbon, titanium oxide ($TiO_2$), aluminum oxide ($Al_2O_3$), silicon oxide ($SiO_2$), zinc oxide ($ZnO_2$), zirconium oxide ($ZrO_2$), manganese oxide ($MnO_2$), iron oxide ($Fe_2O_3$), vanadium oxide ($V_2O_5$), tin oxide ($SnO_2$), tungsten oxide ($WO_3$) and cerium oxide ($CeO_2$). More preferably, as the carrier, the cerium oxide ($CeO_2$) or a composite oxide containing cerium oxide ($CeO_2$) may be used.

The basic solution used in the step a) serves to activate the oxidation reaction of allyl alcohol. The basic solution may be prepared by mixing a basic compound including an alkali metal or an alkali earth metal with water. More specifically, the basic compound may include at least one selected from the group consisting of: sodium hydroxide, lithium hydroxide, potassium hydroxide and calcium hydroxide.

The basic compound included in the basic solution may be used in an amount of 0.01 to 10 mol, preferably, 2 to 5 mol, based on 1 mol of allyl alcohol. The amount of the basic compound used influences the conversion of allyl alcohol and the yield and selectivity of acrylic acid, 3-hydroxypropionic acid (3-HPA) and glyceric acid.

Further, among the products, acrylic acid and 3-hydroxypropionic acid (3-HPA) may be obtained in the form of a salt by the addition of the basic compound.

The gas injected in the step b) may be oxygen-containing gas. In the step b), the reactor is heated to maintain the temperature in the reaction at 30 to 100° C., and simultaneously the oxygen-containing gas is injected, thereby supplying oxygen into the reactor and simultaneously maintaining the partial pressure of oxygen in the reactor at a high pressure of 1 to 50 bar based on absolute pressure during the reaction of the mixed solution. Here, when the temperature in the reactor is lower than 30° C., there is a problem in that the conversion of allyl alcohol is greatly lowered due to the decrease in the oxidation reaction rate thereof. Further, when the temperature in the reactor is higher than 100° C., there is a problem in that the side reaction of allyl alcohol is increased due to the increase in the temperature of the reactor, thus greatly decreasing the selectivity of acrylic acid. Further, the gas injected into the reactor may include oxygen in amount of 10 vol % or more, preferably 20 to 100 vol %, and more preferably 30 to 100 vol %. In this case, when the amount of oxygen included in the gas is less than 10 vol %, there is a problem in that the oxidation reaction rate of allyl alcohol is greatly decreased. Further, when the partial pressure of oxygen in the reactor is less than 1 bar, there is a problem in that the oxidation reaction of allyl alcohol does not easily proceed, and when the partial pressure of oxygen in the reactor is more than 50 bar, there is a problem in that additional effects attributable to pressure rise is not great.

Further, as the reactor used in the step b), a generally-known reactor, such as a batch reactor, a continuous stirred tank reactor (CSTR), a plug flow reactor (PFR) or a fluidized bed reactor, may be used.

The liquid reaction product may be at least one selected from the group consisting of acrylic acid, 3-hydroxypropionic acid (3-HPA) and glyceric acid.

In the step c), the separation of acrylic acid from the liquid reaction product may be carried out by means of acidification, ion exchange, extraction, crystallization, distillation or the like.

The yield of acrylic acid prepared by this method is 30% or more, preferably, 50% or more. Therefore, this method is excellent in terms of economical efficiency.

Further, the method is characterized in that the conversion of allyl alcohol is 70% or more.

Hereinafter, the present invention will be described in more detail with reference to the following Examples. However, these Examples are set forth to illustrate the present invention, and the scope of the present invention is not limited thereto.

Example 1

Preparation of Heterogeneous Catalyst for Preparing Acrylic Acid from Allyl Alcohol 12 mg of $HAuCl_4 \cdot 3H_2O$ was dissolved in 100 mL of distilled water, and then the pH of this solution was adjusted to 10 by using a 0.2 M aqueous sodium hydroxide solution. Thereafter, 190 mg of cerium oxide was dispersed in the resulting solution, stirred at 70° C. for 1, 3, 6 and 12 hours, respectively, filtered, washed and then dried to obtain a catalyst.

Example 2

Preparation of Acrylic Acid from Allyl Alcohol 30 mg of the catalyst prepared by the method of Example 1 was added to a mixed solution of distilled water 17.24 mL, sodium hydroxide 2.07 g and allyl alcohol 1.17 mL, and then the solution was put into a 50 mL glass reactor. This glass reactor was evacuated under vacuum, and then charged with oxygen-containing gas having a pressure of 3 bar. Thereafter, the resulting solution was reacted at 50° C. for 24 hours in the glass reactor. During the reaction of the solution, the pressure of the oxygen-containing gas in the glass reactor was maintained at 3 bar. In this way, a liquid reaction product was obtained. The qualitative and quantitative analyses of the liquid reaction product were carried out using liquid chromatography (LC), respectively.

Experimental Example

The analysis of acrylic acid, 3-hydroxypropionic acid and glyceric acid in the liquid reaction product prepared in Example 2 was carried out by area % using high performance liquid chromatography (YL9100 HPLC, Young Lin Instrument Co.). The conversion of allyl alcohol, the selectivity of acrylic acid and the yield of acrylic acid were calculated using Math Equations 1 to 3, respectively.

Allyl alcohol conversion (%)=100×(allyl alcohol moles before reaction−allyl alcohol moles after reaction)/(allyl alcohol moles before reaction) [Math Equation 1]

Acrylic acid yield (%)=100×(produced acrylic acid moles)/(allyl alcohol moles before reaction) [Math Equation 2]

The selectivity of acrylic acid can be calculated from allyl alcohol conversion and acrylic acid yield data using Math Equation 3.

Acrylic acid selectivity (%)=100×(acrylic acid yield)/(allyl alcohol conversion) [Math Equation 3]

Figure 1B:
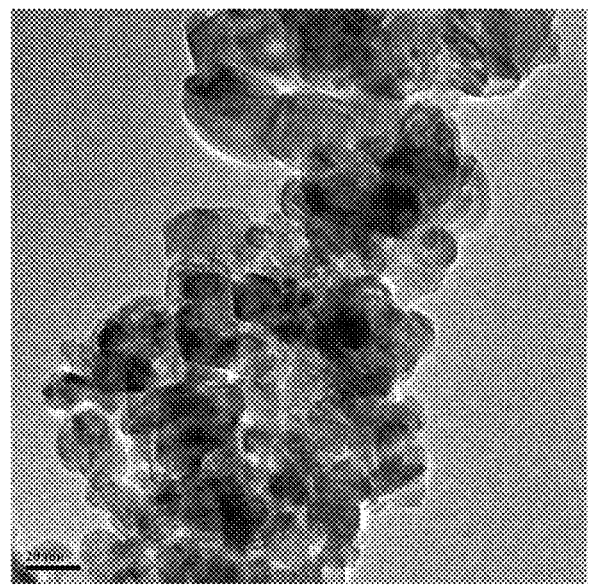
Figure 1C:
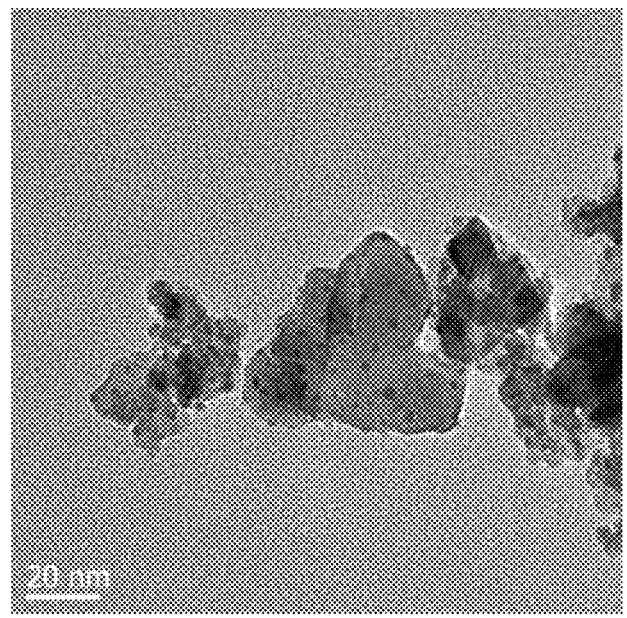
Figure 1D:
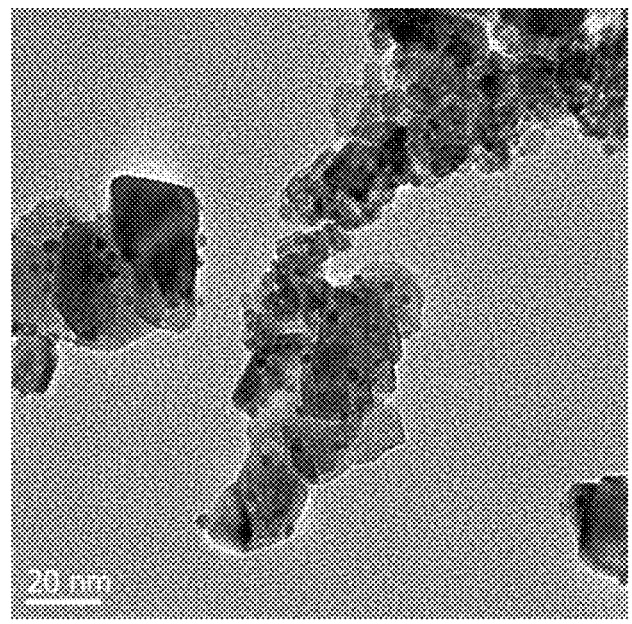

FIGS. 1A to 1D shows the photographs of the heterogeneous catalyst prepared in Example 1, taken using a transmission electron microscope (JEM-2100, JEOL). Here, cerium oxide ($CeO_2$) was used as a carrier, the sizes of gold particles supported in the carrier are shown according to catalyst synthesis time, and the weight percentages (wt %) of gold particles based on the total weight of the carrier are shown, respectively.

Further, the average size of gold particles according to catalyst synthesis time, and the yields of reaction products and the conversion of allyl alcohol according to reaction conditions were measured, and the results thereof are given in Table 1 below. From Table 1, it can be ascertained that each of the yields of acrylic acid and 3-HPA increases as the average size of gold particles decreases. Particularly, it can be seen that, when the average size of gold particles is 1 nm or less, the yield of acrylic acid is 50% or more. Like this, it can be ascertained from the following results that acrylic acid can be directly synthesized from allyl alcohol at a high yield by a one-pot reaction.

TABLE 1

| Catalyst synthesis time (h) | Average size of gold particles (nm) | Conversion (%) | Yield (%) | | |
|---|---|---|---|---|---|
| | | | 3-HPA | Acrylic acid | Glyceric acid |
| 1 | <1 | 100 | 28.4 | 51.1 | — |
| 3 | 1.9 | 100 | 24.1 | 43.1 | — |
| 6 | 2.9 | 100 | 21.7 | 41.4 | — |
| 12 | 3.8 | 100 | 34.4 | 41.0 | — |

T = 50° C.,
[allyl alcohol] = 1M,
NaOH/allyl alcohol = 3,
$pO_2$ = 3bar,
t = 24 h,
solution 18.4 ml,
catalyst ~30 mg Table 2 below shows the test results of determining the optimal reaction time in the method of preparing acrylic acid from allyl alcohol according to the present invention. From Table 2, it can be ascertained that both the yields of 3-HPA and acrylic acid increase until the reaction time reaches 9 hours, but that the yield of 3-HPA greatly decreases and the yield of acrylic acid slightly decreases when the reaction time exceeds 9 hours.

TABLE 2

| Reaction time | Conversion (%) | Yield (%) | | |
|---|---|---|---|---|
| | | 3-HPA | Acrylic acid | Glyceric acid |
| 3 hour | 85.2 | 23.1 | 15.2 | — |
| 6 hour | 96.4 | 38.0 | 36.5 | — |
| 9 hour | 99.3 | 40.9 | 43.8 | — |
| 12 hour | 100 | 37.9 | 41.9 | — |
| 15 hour | 100 | 25.8 | 40.9 | — |
| 24 hour | 100 | 25.4 | 40.1 | — |

T = 50° C.,
allyl alcohol/metal = 4000,
NaOH/allyl alcohol = 3,
$pO_2$ = 3bar,
t = 24 h,
solution 18.4 ml,
catalyst ~30 mg Table 3 below shows the results of reactions when a catalyst was not used or when only a carrier was used. From Table 3, it can be ascertained that, as reaction products, acrylic acid was not produced, and the yield of 3-HPA also was low.

TABLE 3

| | Conversion (%) | 3-HPA | Acrylic acid | Glyceric acid |
|---|---|---|---|---|
| Carbon | 28.1 | 14.6 | — | 4.3 |
| $Al_2O_3$ | 65.5 | 19.5 | — | 15.9 |
| $CeO_2$ | 65.0 | 23.2 | — | 19.0 |
| $Fe_2O_3$ | 100 | 14.4 | — | — |
| $TiO_2$ | 100 | 13.5 | — | 2.0 |
| Blank | 76.6 | 28.9 | — | 35.7 |

Table 4 below shows the results of reactivity when gold nanoparticles was used without a carrier or when gold exists in the form of a salt compound (gold precursor), not in the form of a nanoparticle. From Table 4, it can be ascertained that, as reaction products, acrylic acid was not produced, and the yield of 3-HPA also was low. Further, it can be ascertained that the conversions of reactants were lowered compared to when a catalyst was supported on a carrier.

TABLE 4

| | Conversion (%) | Acrylic acid | 3-HPA | Glyceric acid |
|---|---|---|---|---|
| Au salt | 78.2 | — | — | 21.1 |
| Au NPs | 51.6 | — | 4.6 | 5.3 |
| Au salt on $CeO_2$ | 58.4 | — | 9.4 | 10.7 |

Therefore, it can be ascertained from the above results that, when acrylic acid is prepared from allyl alcohol using a heterogeneous catalyst for preparing acrylic acid from allyl alcohol, acrylic acid can be directly synthesized from allyl alcohol at a high yield through a one-pot reaction compared to conventional method.

As described above, according to the present invention, acrylic acid can be directly synthesized from allyl alcohol by the oxidation reaction of allyl alcohol through a one-pot reaction using a heterogeneous catalyst including a gold supported on a carrier having a particle size of 5 nm or less, and thus acrylic acid can be produced on a commercial scale, thereby remarkably improving the production yield of acrylic acid compared to conventional methods.

Further, according to the present invention, when acrylic acid is produced from allyl alcohol derived from glycerol, acrylic acid can be produced from environment-friendly biodiesel without using fossil fuel, compared to when acrylic acid is produced from propylene obtained from fossil fuel. Therefore, when acrylic acid is produced from allyl alcohol, glycerol, as a by-product of biodiesel, can be effectively used, and thus the economical efficiency of biodiesel can be increased, and acrylic acid can be effectively produced from glycerol.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A heterogeneous catalyst for preparing acrylic acid from allyl alcohol, wherein the catalyst includes gold having a particle size of 5 nm or less supported on a carrier, wherein the carrier is cerium oxide ($CeO_2$) or a composite oxide containing cerium oxide ($CeO_2$).

2. The heterogeneous catalyst of claim 1, wherein the gold has a particle size of 1 nm or less.

3. The heterogeneous catalyst of claim 1, wherein the gold is included in an amount of 5 wt % or less based on a total dry weight of the carrier.

* * * * *